United States Patent [19]

Moroux

[11] Patent Number: 4,637,868

[45] Date of Patent: Jan. 20, 1987

[54] METHOD OF OXIDIZING HYDRAZO COMPOUNDS TO CORRESPONDING AZO COMPOUNDS BY HYDROGEN PEROXIDE

[75] Inventor: Julien Moroux, Lamorlaye, France

[73] Assignee: Societe Francaise d'Organo-Synthese, Gennevilliers, France

[21] Appl. No.: 835,910

[22] Filed: Mar. 4, 1986

[30] Foreign Application Priority Data

Mar. 4, 1985 [FR] France ............................. 85 03147

[51] Int. Cl.$^4$ ............................................. C07C 107/02
[52] U.S. Cl. ................................. 204/157.82; 534/586
[58] Field of Search ..................... 534/586; 204/157.82

[56] References Cited

U.S. PATENT DOCUMENTS

| | | | |
|---|---|---|---|
| 2,469,358 | 5/1949 | Alderson et al. | 534/586 X |
| 2,586,995 | 2/1952 | Robertson | 534/586 X |
| 4,039,527 | 8/1977 | Magaoka et al. | 534/586 X |
| 4,094,868 | 6/1978 | Chendalia et al. | 534/586 X |

FOREIGN PATENT DOCUMENTS

263921 10/1963 Australia ............................. 534/586
48-03821 2/1973 Japan .................................. 534/586

*Primary Examiner*—Charles F. Warren
*Assistant Examiner*—C. S. Greason
*Attorney, Agent, or Firm*—Millen & White

[57] ABSTRACT

This invention relates to a novel method of oxidizing hydrazo compounds to corresponding azo compounds, and more particularly 4,4'-hydrazo-bis-4-cyano-pentanoic acid to 4,4'-azo-bis-4-cyano-pentanoic acid at a temperature close to ambient temperature, said method comprising the step of effecting oxidation with the aid of hydrogen peroxide under the following conditions: catalysis of the reaction by means of UV radiation, operation in aqueous solution at a pH$\leq$0.5, said pH being obtained by addition of hydrochloric acid and/or hydrobromic acid, and operation in a reaction medium comprising Br$^-$ ions at a concentration at least equal to 30 ppm.

4 Claims, No Drawings

METHOD OF OXIDIZING HYDRAZO COMPOUNDS TO CORRESPONDING AZO COMPOUNDS BY HYDROGEN PEROXIDE

The present invention relates to a method of oxidizing hydrazo compounds to corresponding azo compounds, and in particular 4,4'-hydrazo-bis-4-cyanopentanoic acid to 4,4'-azo-bis-4-cyano-pentanoic acid, hereinafter referred to as "azocarboxy".

It is known to prepare the "azocarboxy" from the corresponding hydrazo derivative by carrying out a reaction of oxidation by chlorine, said reaction being catalyzed by traces of bromine.

The use of this polluting oxidizing agent (chlorine) necessitates a complex and expensive installation and is not without danger. In addition, the impure crude product obtained is difficult to isolate by filtration and requires purification, which gives a mediocre chemical yield.

The present invention is based on the discovery that 4,4'-hydrazo-bis-4-cyano-pentanoic acid is oxidizable to corresponding azo by hydrogen peroxide via hydroxyl radicals with a good yield, without requiring expensive purification.

However, it appears that such oxidation by hydrogen peroxide, which must be carried out at a temperature close to ambient temperature taking into account the nature of the reagents and the products obtained, is too slow in order to be applicable on an industrial scale. It has been found, and this is precisely the object of the present invention, that reaction conditions could be found which enabled said oxidation to be usable industrially. These conditions are as follows:

catalyze the reaction by means of a radiation situated in the near ultra-violet, operate in aqueous solution at a pH$\leq$0.5, pH being obtained by addition of hydrochloric acid and/or hydrobromic acid, arrange for the reaction medium to comprise Br$^-$ ions at a concentration at least equal to 30 ppm, and preferably equal to about 0.1%.

As has been stated, the reaction temperature is close to ambient temperature; operation will be carried out between +5° and +40° C. and preferably between +20° and +25° C.

The UV radiation used is formed, as is generally the case industrially, by a source emitting in the wave lengths included between the visible and the wave length (UV) compatible with the material used for making said source. This radiation is useful for provoking decomposition of the hydrogen peroxide added to the medium but also, possibly, for promoting certain other reactions which develop in said medium.

The aqueous solution will comprise between 0.25 and 1 mole of hydrazo per liter and is limited only by practical considerations. The fluidity of the medium is controlled by an anionic surface active agent at a dose which may vary between 0.25 and 1 g/l.

The aqueous reaction medium must have a pH at the most equal to 0.5, said pH being obtained by addition of hydrochloric or hydrobromic acid. The preferred pH is between 0.3 and 0.4.

The Br$^-$ ions are supplied either by the hydrobromic acid when this acid is used as acidifying compound, or by bromides.

The hydrogen peroxide is used in excess with respect to the stoichiometry of the reaction, which involves the use of one molecule of hydrogen peroxide per molecule of hydrazo; the excess hydrogen peroxide may vary between about 25% and an upper limit which is determined solely by economical and practical considerations, the preferred excess being 65%. The hydrogen peroxide may be of any concentration; it is recalled that a 35% hydrogen peroxide is often used in industry. According to the invention, the azo is obtained with a very good yield and with a minimum of purification operations (draining, washing and drying).

The following non-limiting examples illustrate the invention.

EXAMPLE 1

In a 4-necked, 6 l flask provided with a stirrer, a thermometer, a non-immersed nitrogen inlet, a dropping funnel, an evacuation tube and a cooled Heraeus T Q 150 UV lamp, containing 3470 g of aqueous solution of 2 moles of sodium salt of 4,4'-hydrazobis-4-cyanovaleric acid prepared from 464 g (4.00 moles) of levulinic acid, there are introduced 2 g of sodium diisooctylsulfosuccinate, 6 g of sodium bromide and, with stirring at a temperature of between 20° and 25°, 800 g of 37% hydrochloric acid. The final pH of the medium is 0.4.

A slow stream of nitrogen is established and the UV lamp lit up. 320 g (3.30 moles) of 35% hydrogen peroxide are introduced in 1 hour, the temperature being maintained between 20° and 25° C.

A level is maintained in order to terminate the reaction. The reaction is terminated when 1.15 moles of hydrogen peroxide per mole of hydrazo have been consumed, this requiring from 7 to 8 hours.

After draining, washing with water and drying, 440–450 g of 4,4'-azo-bis-4-cyano-pentanoic acid are obtained (yield: 78.5–80.3%). Content of nitrogen capable of being liberated: 9.9–10.0% (Theory: 10.0%).

EXAMPLE 2

Example 1 is repeated, but omitting certain specific means of the invention; the following was obtained:

-2a-

The conditions are the same as in Example 1, except that the UV lamp is not lit up.

24 hours are required to consume 1.11 mole of H$_2$O$_2$. 440 g of azocarboxy-9.9% liberatable nitrogen are isolated.

-2b-

The conditions are the same as in Example 1 except that the quantity of HCl is reduced to 600 g and the UV lamp is not lit up.

After 24 hours, 350 g (yield by weight: 62%) of impure azocarboxy-6.05% liberatable nitrogen are isolated.

-2c-

The conditions are the same as in Example 1, except that the sodium bromide is eliminated.

After 8 hours of reaction, 1.20 moles of H$_2$O$_2$ are consumed and 386 g (yield: 69%) of azocarboxy-10.0% liberatable nitrogen are isolated.

As indicated in Example 1, a very pure "azocarboxy" is obtained. It is recalled that this "azocarboxy" is a water-soluble initiator of polymerization by free radicals. It is also useful as co-reagent for introducing acid -COOH functions into a polymer.

There are reasons to believe that, although the reaction employed according to the invention is probably more complex than appears a priori, this same reaction may be used for the preparation of the azo compounds from the hydrazo compounds. The basic oxidizing conditions: $H_2O_2$, UV radiation, acid pH and possibly complementary catalysis by $Br^-$ ions, must also be employed although certain specific adaptations may prove desirable with a view to obtaining optimal speed and yield.

What is claimed is:

1. A method of oxidizing hydrazo compounds to corresponding azo compounds, and more particularly 4,4'-hydrazo-bis-4-cyano-pentanoic acid to 4,4'-azobis-4-cyano-pentanoic acid at a temperature close to ambient temperature, said method comprising the step of effecting oxidation with the aid of hydrogen peroxide, under the following conditions:

catalysis of the reaction by means of UV radiation, operation in aqueous solution at a $pH \leq 0.5$, said pH being obtained by addition of hydrochloric acid and/or hydrobromic acid, operation in a reaction medium comprising $Br^-$ ions at a concentration at least equal to 30 ppm.

2. The method of claim 1, wherein the reaction is carried out by using an excess of hydrogen peroxide.

3. The method of one of claim 1, wherein the reaction is carried out in the presence of a surface-active agent.

4. The method of claim 2, wherein the reaction is carried out in the presence of a surface-active agent.

* * * * *